(12) United States Patent
Parra et al.

(10) Patent No.: US 6,208,983 B1
(45) Date of Patent: Mar. 27, 2001

(54) METHOD AND APPARATUS FOR TRAINING AND OPERATING A NEURAL NETWORK FOR DETECTING BREAST CANCER

(75) Inventors: Lucas Parra, New York; Paul Sajda, Jersey City; Clay Douglas Spence, Princeton Junction, all of NJ (US)

(73) Assignee: Sarnoff Corporation, Princeton, NJ (US)

(*) Notice: Subject to any disclaimer, the term of this patent is extended or adjusted under 35 U.S.C. 154(b) by 0 days.

(21) Appl. No.: 09/126,341

(22) Filed: Jul. 30, 1998

Related U.S. Application Data
(60) Provisional application No. 60/073,135, filed on Jan. 30, 1998.

(51) Int. Cl.$^7$ .................................................. G06F 15/18
(52) U.S. Cl. ............................... 706/21; 706/16; 706/25
(58) Field of Search ............................... 706/16, 21, 25

(56) References Cited

U.S. PATENT DOCUMENTS

| | | | |
|---|---|---|---|
| 4,955,383 | 9/1990 | Faupel | 600/407 |
| 5,099,844 | 3/1992 | Faupel | 600/372 |
| 5,320,101 | 6/1994 | Faupel | 600/407 |
| 5,427,098 | 6/1995 | Faupel | 600/407 |
| 5,560,357 | 10/1996 | Faupel | 600/345 |
| 5,660,177 | 8/1997 | Faupel | 600/382 |
| 5,678,547 | 10/1997 | Faupel | 600/409 |
| 5,697,369 | 12/1997 | Long, Jr. et al. | 600/407 |
| 5,983,211 | * 11/1999 | Heseltine et al. | 706/15 |
| 6,056,690 | * 5/2000 | Roberts | 600/300 |

OTHER PUBLICATIONS

Polakowski et al, "Computer–Aided Breast Cancer Detection and Diagnosis of Masses Using Difference of Gaussians and Derivative–Based Feature Saliency", IEEE Transactions on Medical Imaging, Dec. 1997.*

Jordan et al, "Hierarchical Mixtures of Experts and the E.M Algorithm", IEEE Proceedings of 1993 International Joint Conference on Neural Networks.*

Chen et al, "A Modified Mixtures of Expert Architecture for Classification with Diverse Features", IEEE International Conference on Neural Networks, Jun. 1997.*

Tam et al., "Integrating Expert Models by Local Receptive Neural Network", IEEE Proceedings of the International Conference on Intelligent Engineering Systems, Sep. 1997.*

Weigend et al, "Modeling, Learning, and Meaning: Extracting Regimes from Time Series", IEEE Meditarranean Electro Technical Conference, May 1996.*

Jacobs et al, "Learning Piecewise Control Strategies in a Modular Neural Network Architecture", IEEE Transactions on System, Man, and Cybernetics, Mar./Apr. 1993.*

Jacobs, Robert A., Jordan, Michael I., Nowlan, Steven J., Hinton, Geoffrey E., "Adaptive Mixtures of Local Experts", Neural Computation 3, pp. 79–87, 1991.

(List continued on next page.)

*Primary Examiner*—George B. Davis
(74) *Attorney, Agent, or Firm*—William J. Burke (57) ABSTRACT

A method and apparatus for training and operating a neural network using gated data. The neural network is a mixture of experts that performs "soft" partitioning of a network of experts. In a specific embodiment, the technique is used to detect malignancy by analyzing skin surface potential data. In particular, the invention uses certain patient information, such as menstrual cycle information, to "gate" the expert output data into particular populations, i.e., the network is soft partitioned into the populations. An Expectation-Maximization (EM) routine is used to train the neural network using known patient information, known measured skin potential data and correct diagnosis for the particular training data and patient information. Once trained, the neural network parameters are used in a classifier for predicting breast cancer malignancy when given the patient information and skin potentials of other patients.

11 Claims, 5 Drawing Sheets

OTHER PUBLICATIONS

Jordan, Michael I., Jacobs, Robert A., "Hierarchical Mixtures of Experts and the EM Algorithm", Neural Computation 6, pp. 181–214, 1994.

Waterhouse, S.R., Robinson, A.J., "Classification using Hierarchical Mixtures of Experts", Proceedings IEEE Workshop on Neural Networks for Signal Processing IV, pp. 177–186, 1994.

* cited by examiner

METHOD AND APPARATUS FOR TRAINING AND OPERATING A NEURAL NETWORK FOR DETECTING BREAST CANCER

This patent application claims benefit of U.S. provisional patent application Ser. No. 60/073,135, filed Jan. 30, 1998 the disclosure of which is incorporated herein by reference.

The invention is related to expert systems and, more particularly, the invention is a method and apparatus for training and operating a neural network to detect breast cancer from skin potential measurements.

BACKGROUND OF THE DISCLOSURE

A device exists in the prior art that measures a series of breast skin surface potentials for the purpose of detecting breast cancer (See U.S. Pat. Nos. 5,697,369; 5,678,547; 5,660,177; 5,560,357; 5,427,098; 5,320,101; 5,099,844; and 4,955,383, each of which is incorporated herein by reference). In addition to the device for collecting skin surface potential data, the prior art also teaches several techniques for using these skin surface potentials to predict the likelihood of breast cancer. In particular, U.S. Pat. No. 5,697,369 teaches using a neural network to process skin surface potential data to detect cancer in a suspect skin region. However, noise and confounding physiological signals make the training task for a neural network a particular challenge for use in predicting breast cancer.

Figure 1:
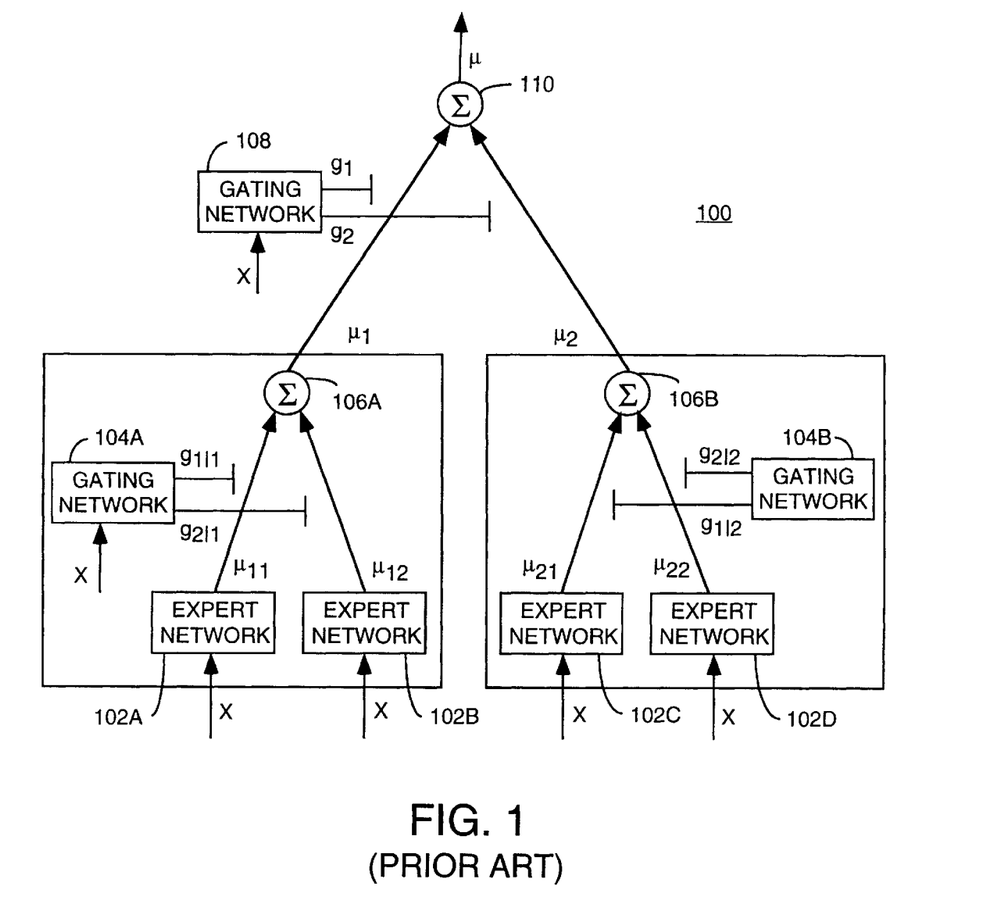
FIG. 1 depicts a functional block diagram of a neural network having a mixture of experts in accordance with the prior art.

Various other forms of neural network architectures exist such as those disclosed in Jacobs et al. "Adaptive Mixtures of Local Experts," Neural Computation, Vol. 3, pp. 79–87 (1991); Waterhouse et al., "Classification Using Hierarchical Mixtures of Experts," Proc. 1994 IEEE on Neural Networks for Signal Processing IV, pp. 177–186 (1994); and Jordan et al., "Hierarchical Mixtures of Experts and the EM Algorithm," Neural Computation, Vol. 6, pp. 181–214 (1994), which are hereby incorporated herein by reference. FIG. 1 depicts a functional block diagram of a two-level hierarchical mixture of experts for a neural network 100 in accordance with the prior art. This architecture uses a plurality of hierarchically arranged expert networks 102A–102D (experts) to classify input data x. Gating networks 104A and 104B process the output result from each expert network 102A–102D using a gating parameter g. The gated expert results are then summed (in combiners 106A and 106B) at a node of the neural network. The results are then gated by gating network 108 and coupled to the next summing node 110. In this manner the data (represented as vector x) is used to control both the gates and the experts. Each of the gates apply a weighting values to the expert outputs where the weighting values depend upon the input vector x such that the neural network 100 operates non-linearly. The use of weighted gating forms a network that uses "soft" partitioning of the input space and the expert networks provide local processing within each of the partitions. The soft partitioning network can be trained using an Expectation-Maximization (EM) algorithm.

Heretofore a neural network containing a mixture of experts has not been applied to the complex data set of skin potential data and patient information to detect breast cancer. Therefore, there is a need in the art for an improved method and apparatus for training and operating a neural network to provide an accurate technique for breast cancer detection.

SUMMARY OF THE INVENTION

The present invention is a method and apparatus for training and operating a neural network to detect breast cancer malignancy by analyzing skin surface potential data. In particular, the invention uses certain patient information, such as menstrual cycle information, to "gate" the expert output data into particular populations, i.e., the data is soft partitioned into the populations upon which different expert networks operate. An Expectation-Maximization (EM) routine is used to train the neural network using known patient information, known measured skin potential data and correct diagnoses for the particular training data and patient information. Once trained, the neural network parameters are used in a classifier for predicting breast cancer malignancy when given the patient information and skin potentials of other patients.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 2:
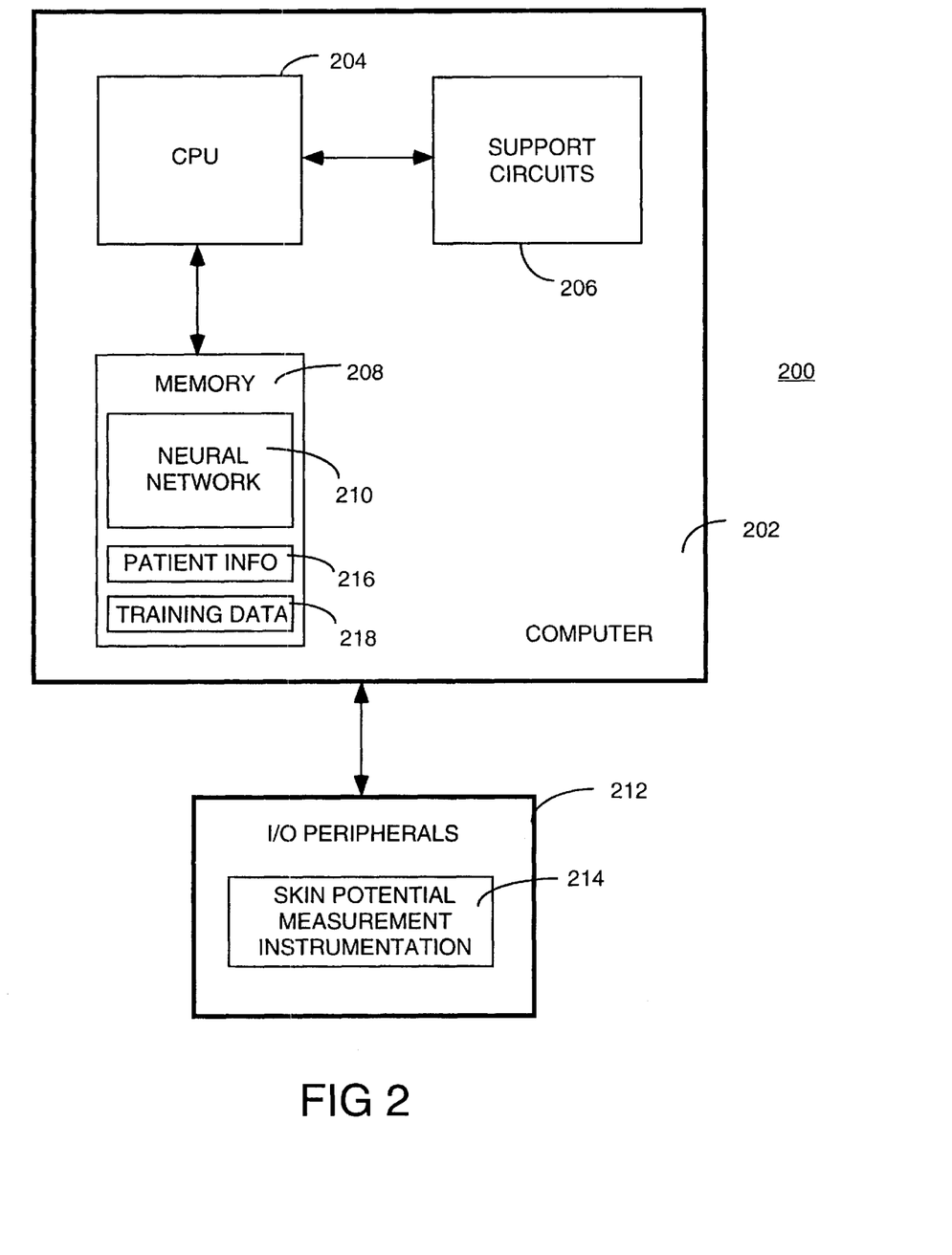
FIG. 2 depicts a computer system that is used to implement the present invention.

FIG. 2 depicts a general purpose computer system 200 containing a computer 202 and Input/Output (I/O) peripherals 212. The computer 202 contains a central processing unit (CPU) 204, support circuits 206 and memory 208. The support circuits 206 include conventional circuits such as cache, clock circuits, analog-to-digital converters, power supplies, and the like. The CPU 204 can be one of any readily available high-power processors such as a PENTIUM II available from Intel Corporation of Santa Clara, Calif. The memory 208 can be any digital storage medium including a hard disk, random access memory (RAM), read only memory (ROM), floppy disk, tape cartridge or any combination thereof. The memory stores a program 210 that, when executed, forms the neural network and causes the computer system 200 to perform the breast cancer diagnosis method of the present invention. The memory 210 also stores data such as patient information 216 and training data 218 including training diagnosis information and training skin surface potentials that are used to train the neural network.

The I/O peripherals 212 contain conventional equipment such as a keyboard, mouse and display unit as well as skin potential measurement instrumentation. Such measurement instrumentation is well known in the art and disclosed in U.S. Pat. Nos. 5,678,547; 5,660,177; 5,560,357 and 5,427,098 and hereby incorporated herein by reference.

In the illustrative embodiment of the invention, the invention uses a mixture of experts architecture to process surface potential measurement(s) in combination with patient information to train and operate a neural network. Such a mixture of experts architecture for the neural network of the present invention is depicted as a functional block diagram in FIG. 3.

Figure 3:
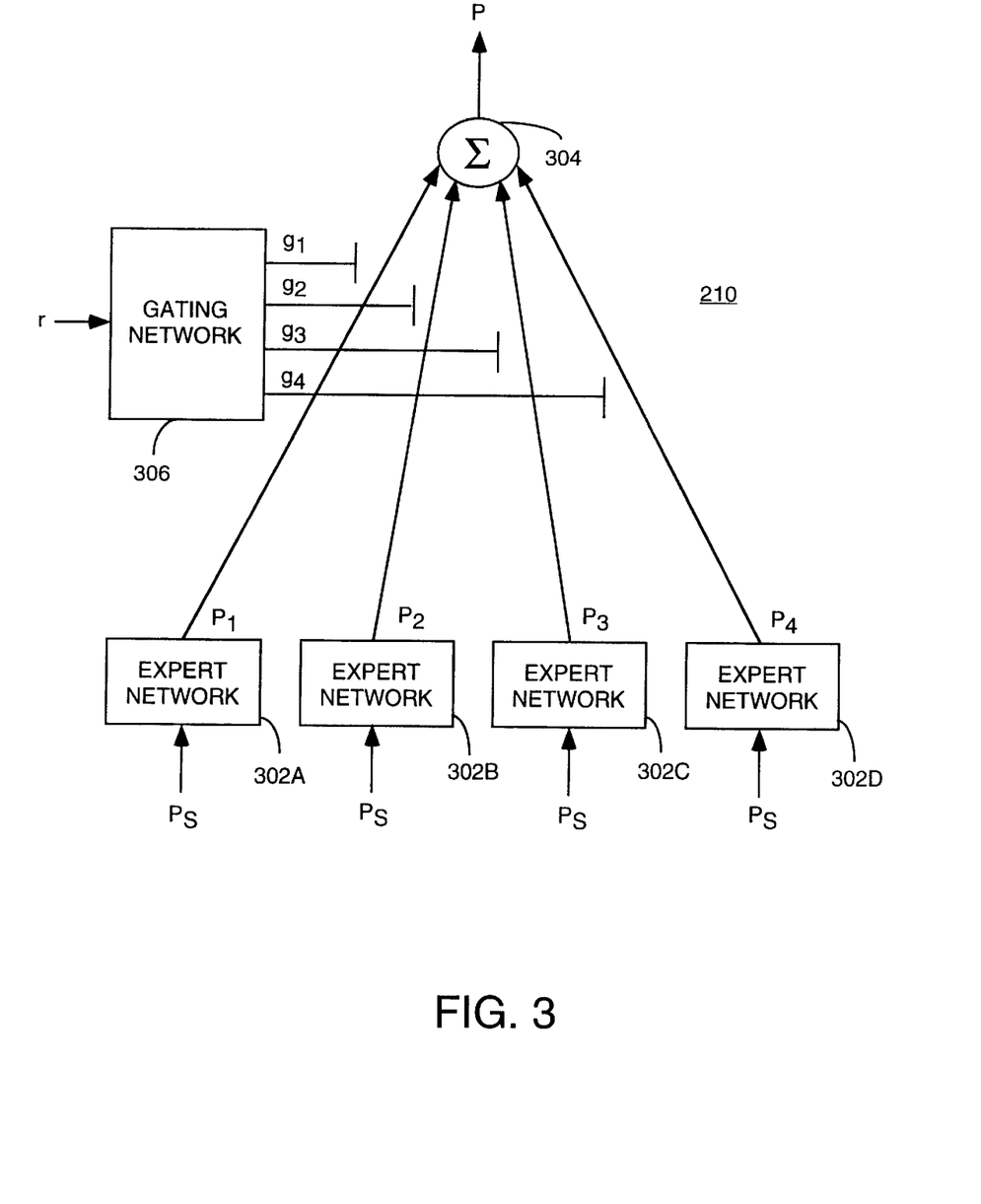
FIG. 3 depicts a functional block diagram of a neural network having a mixture of experts in accordance with the present invention.

The neural network 210 of the present invention contains a plurality of experts 302A–D that are used to classify data $P_s$. As gating network 306 processes the output of each expert network 302A–D using gating weights $g_n$. The gating weights are derived from a set of patient information r. The gated expert results are combined (summed) in combiner 304 to produce result p.

Figure 4:
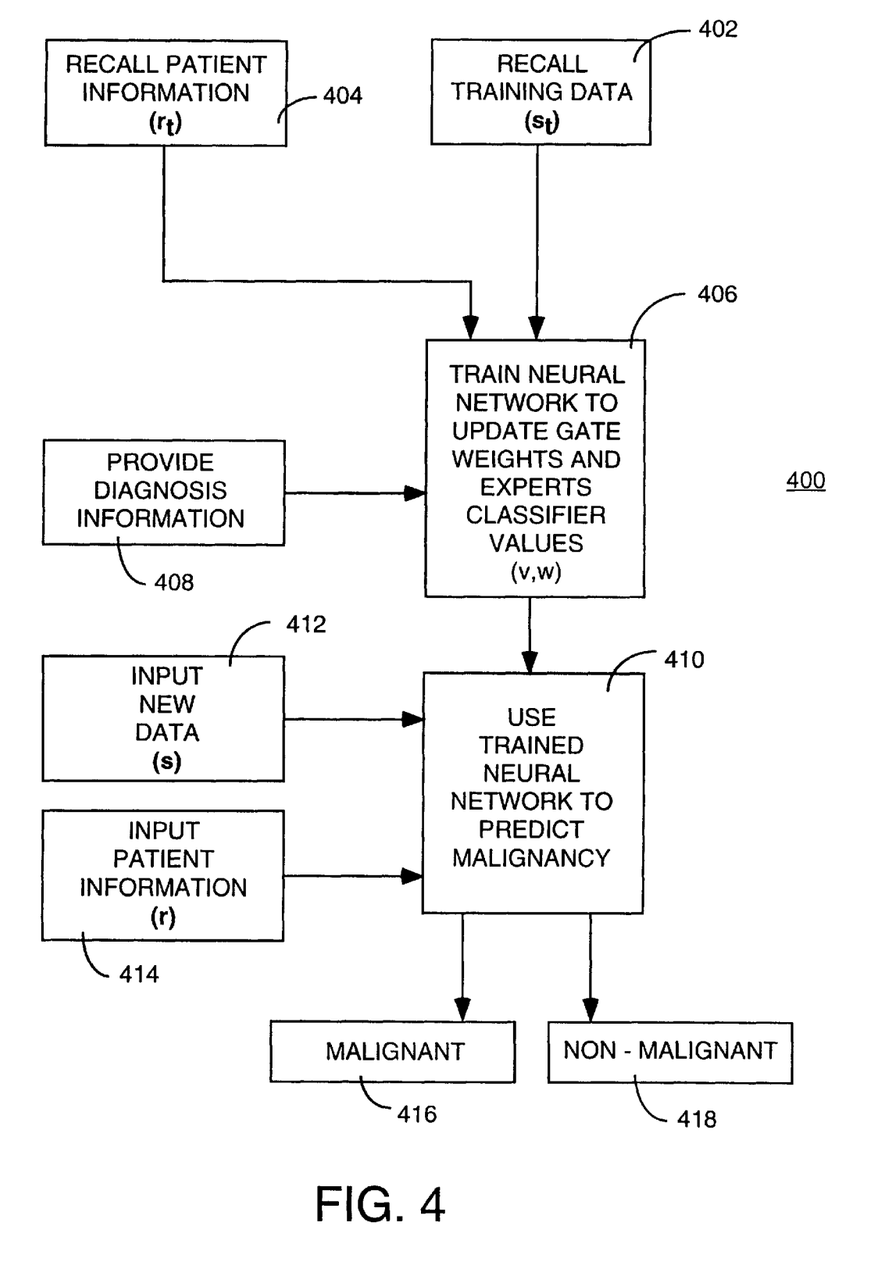
FIG. 4 is a flow diagram of a process of the present invention that is performed by the computer system of FIG. 2.

FIG. 4 depicts a flow diagram of the process 400 of the present invention that trains and utilizes the architecture of FIG. 3 to diagnose breast cancer from a combination of skin potential measurements and patient information. Simply stated, the present invention trains individual experts (classifiers) within the expert architecture of the neural network 210 to discriminate cancer from non-cancer by using a particular subset of the population of training examples. The training data is a set of skin potential measurements that are collected from a known lesion. The training data is generally stored in the memory 208 until recalled in step 402 of routine 400. The partitioning of the training data into different populations, or "gating" of the training data, is based on gating weights. In breast cancer detection, the gating weights are derived from patient information including menstrual cycle, age, family history, and the like. In the following description, the patient information is represented by the vector r (patient information used in training is represented by $r_t$), each of the individual gating weights that modulate each expert output is represented by the variable $g_i$ and the surface potential data is represented by the vector s (skin surface potential data used in training is represented by $s_t$),.

The patient information $r_t$ is stored in memory 208 until recalled at step 404 for use by the CPU 204.

The training data $s_t$ is recalled from memory at step 402 and is used in combination with the patient information $r_t$ to train the neural network at step 406. To properly train the neural network, diagnosis information is provided, at step 408, to the training process. As such, the training process can compare its decisions with actual (correct) decisions to "learn" as the training data is processed by the neural network. As discussed in detail below, the training process updates both the expert parameters and the gating parameters of the neural network, i.e., variables v and w, respectively.

Once trained, the network is used, at step 410, to analyze new skin surface potential data s (input at step 412) using patient information r (input at step 414) that is associated with the new patients. In response to the new data s, the neural network produces a probability as to whether the new data represents malignancy (output 416) or non-malignancy (output 418).

More specifically, during processing of new data, each expert classifier computes a likelihood $p_i$ that data s corresponds to a positive diagnosis. The likelihoods are weighted by the gating weights $g_i$ and added at each neural network node to provide a single likelihood value p for malignancy. This architecture is modeled mathematically as:

$$p = \sum_i g_i(r) p_i(s) \tag{1}$$

Different types of gates and experts are possible, including hierarchical linear gates and/or experts or nonlinear neural network architectures for each expert. Also, the number of experts may vary, depending on the amount of available training examples.

The current embodiment of the invention uses linear "softmax" gates and logistic linear classifiers as experts defined as follows:

$$p_i(u) = \frac{\exp(w_i^T s)}{1 + \exp(w_i^T s)} \tag{2}$$

$$g_i(r) = \frac{\exp(v_i^T r)}{\sum_k \exp(v_k^T r)} \tag{3}$$

The parameter vectors $w_i$ and $v_i$ of the i'th expert and gate, respectively, are determined by training the network as described below.

In the current embodiment, the experts are trained (at step 406) using a series of skin surface potentials measured over the presumed center of a palpable lesion SC, the potential SV, located vertically above or under that center, the median Â of the potentials measured on the asymptomatic breast, and the age of the subject, i.e. $s_t$=[SC, SV, Â, age]. Additional variables may be used as input data within the vector $s_t$ including family history, level of suspicion of cancer from a prior mammographic exam, and the like. The gating weights are generally defined by the day of the skin potential measurement exam relative to the beginning of the menstrual cycle, i.e., r=[mens]. As mentioned previously, one may include other patient information in the vector $r_t$.

Figure 5:
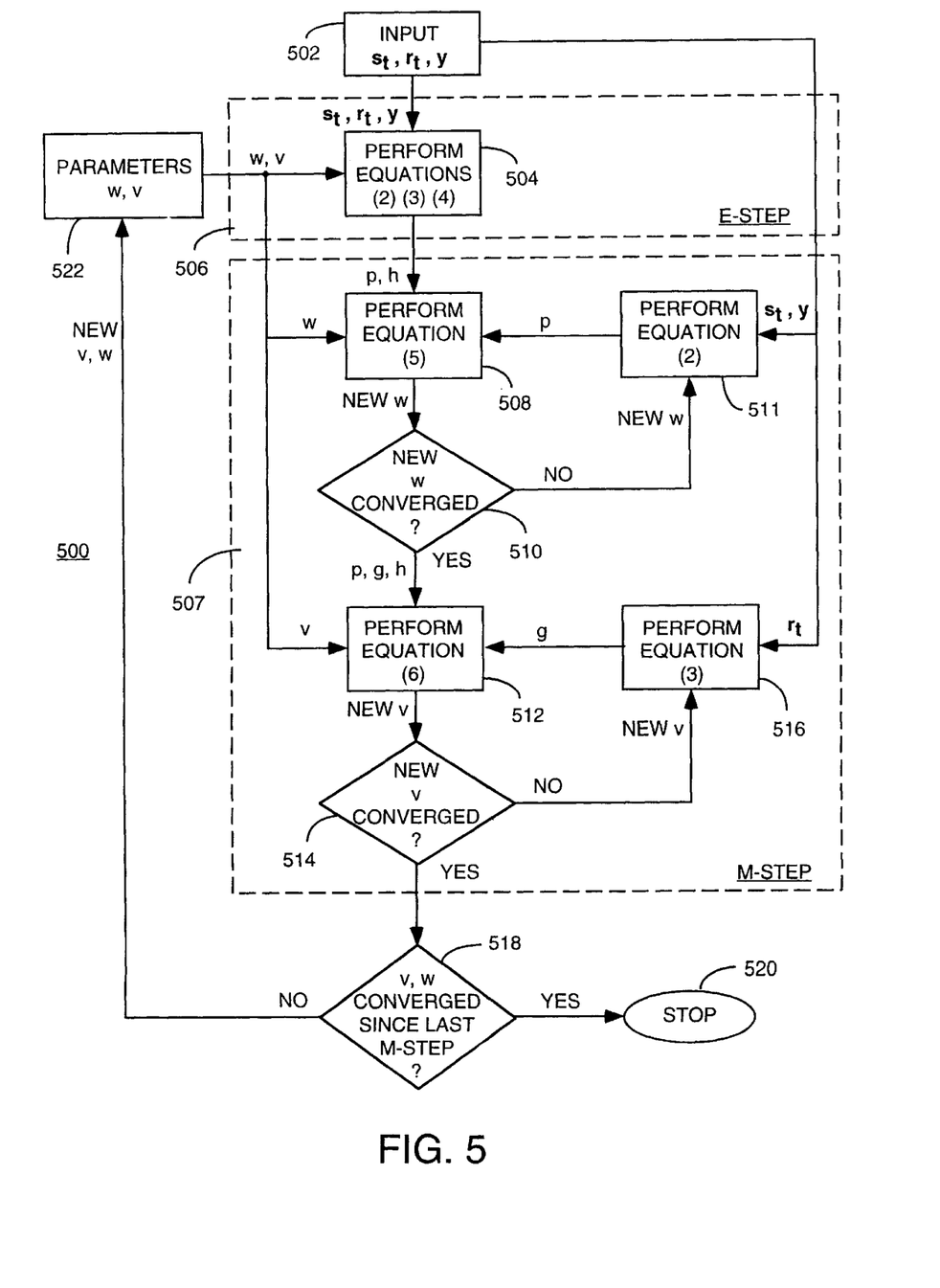
FIG. 5 is a flow diagram of a training routine used be the present invention.

The training algorithm outlined in the Jordan et al. paper (cited above) is the same as that used in the present invention, i.e., an Expectation-Maximization (EM) routine which maximizes (the M-step) using iteratively re-weighted least squares (IRLS) for the experts $w_i$ and gate parameters $v_i$. FIG. 5 depicts a flow diagram of the EM routine 500 that implements the training step 406 of FIG. 4. For the training population, the invention is provided at step 502 the vectors $s_t$ and $r_t$ as well as actual (correct) diagnosis information corresponding to the training data, denoted by y∈ {0, 1}. From $s_t$, $r_t$, and y, step 504 computes probabilities $p_i$ using equation 2 and 3 above and computes the posterior probability $h_i$ that a sample ($s_t$, $r_t$, y) is drawn from a binomial distribution corresponding to expert i, and not the other experts after observing the true classification y using, $$h_i = \frac{g_i(r) p_i(y, s)}{\sum_k g_k(r) p_k(y, s)} \tag{4}$$

where $p_i(1, s_t)=p_i(s_t)$, $p_i(0,s_t)=1-p_i(s_t)$, and $g_i p_i$ as defined in equations (3) and (2) above. Computing this expectation represents the E-step 506 of the EM algorithm. Next, the M-step 507 is performed. Using these posteriors $h_i$, at step 508, the invention can now maximize the likelihood of the observations with respect to the expert classifier parameters $w_i$ and the gating parameters $v_i$ independently. In both cases, the invention uses an IRLS iteration. For the experts this corresponds to, $$A_i = \text{diag}(p_i(1-p_i)h_i)$$
$$w_i^{new} = w_i^{old} + (S^T A_i S)^{-1} S^T A_i (y - P_i) \quad (5)$$

Here the matrix $S=[s_1, \ldots, S_N]$ contains all N training vectors $s_i$ in its columns. Correspondingly, the column vector $y=[y_1, \ldots, Y_N]^T$ represents the known diagnosis for all N subjects, and the vector $p_i$ and $h_i$ are the probabilities computed in equations (2) and (4) for all subjects for the i'th expert. After computing new parameters $w_i$ with equation (5), at step 510, the routine queries whether the new values of $w_i$ are sufficiently converged. If the query is negatively answered, the invention recomputes (at step 511) the probabilities $p_i$ with equation (2) while keeping $h_i$ constant. These updates are iterated through step 508, 510 and 511 until $w_i$ converges for the given $h_i$. Once $w_i$ convergence has been obtained, the routine proceeds to step 512 where a similar iterative procedure is followed to converge the gating parameters $v_i$, $$B_{ij} = (b_{kl})_{ij} = \left( \sum_{t=1}^{N} \delta_{ik} p_{it} - p_{it} p_{kt} r_{lt} r_{jt} \right) \quad (6)$$
$$v_{ij}^{new} = v_{ij}^{old} + \sum_{kl} (B_{ij})_{kl}^{-1} (h_k - g_k) r_l$$

At step 514, the routine queries whether the parameters $v_i$ have sufficiently converged. Here again the invention iterates equations (3) (at step 516) and (step 512) recomputing probabilities $g_k$ of all subjects for every new set of parameters $v_{ij}$ until convergence, while keeping the posteriors $h_i$ constant. When the query at step 514 is affirmatively answered, the M-step 507 of the EM algorithm is completed. At step 518, the routine 500 queries whether both the parameters w and v have converged. If the query is affirmatively answered, the routine stops at step 520. However, if the routine has not converged the new parameters w and v are routed to step 522 to be used in steps 504, 508 and 512 to further iterate and converge the parameters v and w.

Returning to FIG. 4, after training is completed on a representative population for which a true diagnosis was available, the invention, in step 410, can use the trained parameters $w_{ij}$ and $v_{ij}$ to build a classifier for predicting breast cancer from new cases. At step 412, the electrical potentials s are measured for a new subject and together with the patient information r, (input at step 414) the invention computes the likelihood for malignancy using equations (1)–(3).

Although various embodiments which incorporate the teachings of the present invention have been shown and described in detail herein, those skilled in the art can readily devise many other varied embodiments that still incorporate these teachings.

What is claimed is:

1. A method for using a neural network containing a mixture of experts to predict breast cancer from skin surface potentials comprising the steps of:

recalling training data containing skin surface potentials, training patient information containing menstrual cycle information for each patient, and a known correct diagnosis for the training data;

using the training data, training patient information and the known diagnosis to train a gating network and a plurality of expert networks;

applying new data containing skin surface potentials to the expert networks;

applying new patient information corresponding to the new data to the gating network; and     determining a probability that the new data represents malignant breast cancer using trained gating network and expert networks.

2. The method of claim 1 wherein the gating network is trained by deriving a set of gating parameters for the neural network.

3. The method of claim 1 wherein the training step further comprises the steps of:

(a) computing gating weights and expert classifier values;

(b) computing posterior probabilities using the gating weights and the expert classifier values;

(c) jointly maximizing the likelihood of the training data with respect to gating parameters and expert parameters;

(d) iterating through steps (a), (b) and (c) until the gating parameters and expert parameters each converge.

4. The method of claim 1 wherein the training step further comprises the steps of:

(a) using initial values for gating parameters and expert parameters, computing gating weights, expert classifier values, and posterior probabilities;

(b) performing an iteratively re-weighted least squares with respect to the expert parameters while maintaining constant posterior probabilities to converge the expert parameters by generating new expert parameters; and     (c) upon convergence of the expert parameters, performing iteratively re-weighted least squares with respect to the gating parameters while maintaining constant posterior probabilities to converge the gating parameters by generating new gating parameters;

(d) if the gating parameters and expert parameters are not sufficiently converged after performing steps (a), (b) and (c), repeating steps (a), (b), and (c) using the new gating parameters and the new expert parameters as the initial values of the gating parameters and expert parameters.

5. A digital storage medium containing a program that, when executed by a general purpose computer, causes the computer to perform a method for using a neural network containing a mixture of experts to predict breast cancer from skin surface potentials comprising the steps of:

recalling training data containing skin surface potentials, training patient information containing menstrual cycle information for each patient, and a known correct diagnosis for the training data;

using the training data, training patient information and the known diagnosis to train a gating network and a plurality of expert networks;

applying new data containing skin surface potentials to the expert networks;

applying new patient information corresponding to the new data to the gating network; and     determining a probability that the new data represents malignant breast cancer using trained gating network and expert networks.

6. The digital storage medium of claim 5 wherein the gating network is trained by deriving a set of gating parameters for the neural network.

7. The digital storage medium of claim 5 wherein the training step further comprises the steps of:

(a) computing gating weights and expert classifier values;

(b) computing posterior probabilities using the gating weights and the expert classifier values;

(c) jointly maximizing the likelihood of the training data with respect to gating parameters and expert parameters;

(d) iterating through steps (a), (b) and (c) until the gating parameters and expert parameters each converge.

8. The digital storage medium of claim 6 wherein the training step further comprises the steps of:

(a) using initial values for gating parameters and expert parameters, computing gating weights, expert classifier values, and posterior probabilities;

(b) performing an iteratively re-weighted least squares with respect to the expert parameters while maintaining constant posterior probabilities to converge the expert parameters by generating new expert parameters; and (c) upon convergence of the expert parameters, performing iteratively re-weighted least squares with respect to the gating parameters while maintaining constant posterior probabilities to converge the gating parameters by generating new gating parameters;

(d) if the gating parameters and expert parameters are not sufficiently converged after performing steps (a), (b) and (c), repeating steps (a), (b), and (c) using the new gating parameters and the new expert parameters as the initial values of the gating parameters and expert parameters.

9. A neural network containing a mixture of experts to predict breast cancer from skin surface potentials comprising:

a memory for storing training data containing skin surface potentials, training patient information containing menstrual cycle information for each patient, and a known correct diagnoses for the training data;

a processor for recalling the stored training data, training information and diagnoses and using the training data, training patient information and the known diagnoses to train a gating network and a plurality of expert networks;

means for applying new data containing skin surface potentials to the expert networks and for applying new patient information corresponding to the new data to the gating network; and said processor determines the probability that the new data represents malignant breast cancer using the trained gating network and expert networks.

10. The apparatus of claim 9 wherein the gating network is trained by deriving a set of gating parameters for the neural network.

11. The apparatus of claim 9 wherein the processor further comprises:

(a) means for computing gating weights and expert classifier values;

(b) means for computing posterior probabilities using gating parameters and expert parameters;

(c) means for jointly maximizing the likelihood of the gating parameters and the expert parameters;

(d) means for iterating through steps (a), (b) and (c) until the gating parameters and expert parameters each converge.

* * * * *